United States Patent [19]

Kiesele et al.

[11] Patent Number: 5,126,035
[45] Date of Patent: Jun. 30, 1992

[54] ELECTROCHEMICAL MEASURING CELL

[75] Inventors: Herbert Kiesele, Lübeck; Jürgen Tewes, Dortmund; Wolfgang Ehrfeld, Karlsruhe; Dirk Schmidt, Stutensee, all of Fed. Rep. of Germany

[73] Assignee: Dragerwerk Aktiengesellschaft, Fed. Rep. of Germany

[21] Appl. No.: 448,330

[22] Filed: Dec. 11, 1989

[30] Foreign Application Priority Data

Dec. 10, 1988 [DE] Fed. Rep. of Germany ....... 3841621

[51] Int. Cl.$^5$ .............................................. G01N 27/26
[52] U.S. Cl. .................................. 204/415; 204/414; 204/153.17
[58] Field of Search .................... 204/414, 415, 153.17

[56] References Cited

U.S. PATENT DOCUMENTS 4,988,429 1/1991 Mathiessen ........................ 204/415
4,997,541 3/1991 Kiesele et al. ..................... 204/415

Primary Examiner—John Niebling
Assistant Examiner—Bruce F. Bell

[57] ABSTRACT

The invention is directed to an electrochemical measuring cell for detecting gaseous components with an electrolyte which is disposed between a counter electrode and a measuring electrode provided with gas permeable pores. The pores are configured as channels partially or completely filled with the electrolyte and these channels have a diameter which does not exceed 10 micrometers with a channel length of up to 300 micrometers and a web thickness of not more than 5 micrometers. With this configuration, drift and memory effects are suppressed and the measuring sensitivity is increased and, on the other hand, the response time and the residual current are reduced. When the measuring cell is used as a dosimeter, the counter electrode and the measuring electrode are decoupled with respect to a mass transport in the electrolyte.

19 Claims, 1 Drawing Sheet

ELECTROCHEMICAL MEASURING CELL

FIELD OF THE INVENTION

The invention relates to an electrochemical measuring cell for detecting gaseous components with an electrolyte which is disposed between a counter electrode and a measuring electrode provided with pores which are permeable to gas.

BACKGROUND OF THE INVENTION

An electrochemical measuring cell of the kind referred to above is described in published German patent application DE-OS No. 3,609,402. In this known measuring cell, the gas molecules to be detected penetrate through the pores of the measuring electrode up to a gel-like electrolyte and effect an electrochemical reaction at the three-phase boundary defined by the electrode-gelelectrolyte-gas. The electron transfer connected therewith effects a current flow which is a measure of the concentration of the gas to be detected. For this amperometric operating sensor, the characteristics are substantially determined by the geometry of the sensor head in addition to the pure material characteristics of the membrane, electrode and electrolyte. The detection component (or measurement species) does not completely react in the pore channels for the short pore length to cross section ratios. The detection component can dissolve in the electrolyte chamber and trigger drift effects and/or memory effects via back-diffusion. Furthermore, the unfavorable ratio between the active measuring surface and the electrolyte-covered electrode surface leads to an unnecessarily high residual current. The large pores lying far apart from each other lead to a small effective measuring surface from which a low surface-related sensor sensitivity results. A relatively thick foil is used as a diffusion membrane in the sensor referred to above and this leads to high response times and a reduced measuring sensitivity.

SUMMARY OF THE INVENTION

It is an object of the invention to improve a measuring cell of the kind referred to above such that the following is obtained: a suppression of drift and memory effects, an increased measuring sensitivity and a reduction of the response time as well as the residual current value.

According to a feature of the electrochemical measuring cell of the invention, the pores are configured as channels at least partially or even completely filled with the electrolyte. These channels have a diameter of not more than approximately 10 micrometers with a channel length of up to 300 micrometers with the length of the channels being preferably up to 50 micrometers. The web thickness of the channels is not more than 5 micrometers.

The advantages of the invention lie essentially in the improved mass transport characteristics. For the selected large length-diameter ratios, the measuring species reacts virtually completely in the pore channels and in this way they cannot become enriched in the electrolyte chamber. Drift and memory effects are substantially suppressed in this manner.

With the structuring of the channels in the micrometer range, uniform and short diffusion paths are provided in the electrode which lead to short rise times. The well-defined surface geometry leads to uniformly adjustable sensor sensitivities and permits, by means of the selection of the number of channels of the electrode, the quantitative adjustment of the sensor sensitivity during manufacture while retaining the outer electrode dimensions. With the use of small web thicknesses, a favorable ratio of signal to residual current and a higher surface-related sensitivity is obtained by means of the now large channel surface density obtainable and the small electrode end face which is not exposed to the gas to be measured.

The electrode structures described above can be produced by means of suitable microstructure processes such as the LIGA-process. The LIGA-process is a combination of X-ray lithography and galvanoforming. In this connection, reference may be made to U.S. Pat. No. 4,661,212 and the article entitled "Fabrication of microstructures with high aspect ratios and great structural heights by synchrotron radiation lithography, galvanoforming, and plastic moulding (LIGA process)" by E. W. Becker et al, in the publication Microelectronic Engineering 4 (1986), pages 35 to 56.

A microstructure form obtained with the LIGA process permits wall surfaces of the channels which are reproducible in an especially advantageous manner and extend uniformly. An especially low diameter-to-length ratio of 1:3 to 1:30 can be obtained. The openings shown in published German patent application DE-OS No. 3,609,402 can be produced with the aid of etching techniques or by means of photolithography for corresponding pore diameters only to a diameter-length ratio of 1:1. In this connection, reference may be made to the specification sheet M-3011 3.5 M 686 of the Metrigraphics Division of Dynamics Research Corporation of Wilmington, Mass. The electrode material can be nickel or gold; however, an especially cost-effective configuration is provided by a carbonized plastic structure.

The electrolyte filled into the measuring cell can be either polymer, gel-like or even liquid, organic or hydrous. The advantageous operation of the measuring cell having the microstructured measuring electrode is independent of the electrolyte. Uniform and short diffusion paths are provided in the electrolyte by means of the defined electrode structure. Because of the advantageous geometric ratios, a good mass transfer in the region of the boundary surface between the measuring electrode and the electrolyte is provided on the one hand and between the measuring electrode and the electrolyte chamber on the other hand; that is, because of the electrochemical measuring reaction or because of the exchange of the solvent possibly present in the electrolyte with the gas phase, specific concentration changes become effective only to a low degree. Because of this characteristic, the electrolyte on the channels can be applied for mass transport control so that a very thin membrane for a possible covering of the electrode with respect to the ambient can be utilized. In this way, higher sensitivities and shorter response times are obtained.

A hydrophobic covering is preferably stretched over the electrode surface on the gas side so that the end faces of the channel webs carry a cover which can better hold back a liquid or gel-like electrolyte because of the capillary forces. Since only a small plastic mass as adequate, only a small quantity of measuring gas can be stored therein. Furthermore, mechanical deformations are less of a problem than with a membrane-like covering.

However, to provide better protection against dust particles or other foreign bodies which could penetrate into the channels or clog them, the covering is configured as a membrane which covers the channel openings. The mass transport for a given electrolyte is determined to an increasing measure by the channel geometry with a decreasing membrane thickness. The length of the effective diffusion path is dependent substantially on the channel diameter for an adequately thin membrane. Response times beneath one second are obtainable in aqueous electrolytes for channel diameters of less than 10 micrometers. For this purpose, channel lengths of approximately 50 micrometers are suitable.

Polymerization is a method which is suitable for applying very thin pore-free membranes. For membrane deposition, the channels are first filled with a matrix structure or a mold piece which is again withdrawn after forming the membrane. If the channel openings toward the gas end are closed by means of a membrane, an electrolytic film is prevented from forming between the end face of the channel webs and the membrane. A membrane spread over the channel would permit microscopic electrolytic layers which would permit undefined additional reaction surfaces to form next to the inner walls of the channels.

A reagent is added to the electrolyte which goes into a reaction with the gas to be detected. This increases the sensitivity of the measuring cell and stabilizes and maintains this increased sensitivity also for partial activity loss of the electrode surface as well as increases the selectivity of the measuring cell to different gas components. Such additives are advantageously a porphyrin complex or also a phthalocyanine complex with cobalt porphyrin being provided to detect oxygen.

When a reagent of the kind described above is added to the electrolyte, primary products are first formed by the selective reaction of the gas molecules to be detected with the reagent. In a secondary reaction, the primary products are transformed into secondary products on the electrode surface. In this way, the gas molecules can react in the electrolyte with the reagent immediately upon entry of the gas to be detected without these molecules first having to reach the measuring electrode surface in order to bring about a measurable reaction as would be necessary for an electrolyte without a reagent additive. In this way, a steeper concentration gradient is obtained on the overall membrane surface which leads to an increase in sensitivity. The reaction capability of the gas molecules with the reagent is maintained even with the occurrence of a partial contamination of the measuring electrode surface so that the activity loss is only partially transmitted to the detection sensitivity of the measuring electrode.

The selectivity of the measuring cell can be increased by the selection of a suitable reagent which reacts specifically with a gas to be detected. Accordingly, and for the selective measurement of oxygen for example, the cobalt porphyrin is suitable as a reagent. Preferably, the oxygen molecules diffusing into the electrolyte can form a primary reaction product with the cobalt porphyrin.

If the reagent is applied as an inner coating to the channel walls, then the region for producing the primary reaction products is advantageously brought to the vicinity of the reaction surface.

A mechanically especially stable measuring cell which is robust in use is obtained if the measuring and counter electrodes are produced in the same manufacturing process and made from the same structure and packed together in a sandwich-like manner with a polymer electrolyte in the center. In this way, an easily manipulable measuring cell secure against leakage is obtained which has the same good measuring characteristics as other more complex configured measuring cells. The measuring electrode as well as the counter electrode are in communication with the ambient so that especially for oxygen measurements, the oxygen formed to water at the measuring electrode in the electrolyte is reduced to oxygen at the counter electrode and again given off to the ambient. This prevents an enrichment of water in the electrolyte.

If an electrolyte in the measuring cell is provided with an additive in the form of a reagent which can go into an irreversible reaction with the gas to be detected and whose measuring electrode is decoupled from the counter electrode with respect to a mass transport as well as with respect to the reagent and the primary reaction product in the electrolyte, then an electrochemical measuring cell of this kind can also be utilized as a sampling device or dosimeter. With the above-mentioned measures, the condition is prevented that reagent molecules or primary reaction products reach the counter electrode during the taking of the sample. Such a device can be utilized to determine the time-weighted concentrations of the measured gas in the ambient of the person carrying the device.

For the above purpose, and for non-polarized electrodes, the gas being measured is permitted to react with the reagent to form the primary products which are accumulated in the measuring cell for a given time. After the collection time is ended, the electrodes are connected to a voltage source and the primary products are transformed electrochemically into the secondary products. The coulometrically determined charge is a measure for the quantity of gas collected in the collection time.

Narrow channels with a length up to 300 micrometers are preferably used to assure an evaluation time in the range of seconds and to assure an adequate reagent capacity. It is especially advantageous to select a substance as a reagent which reacts with the detection material to form such a primary product which is again formed back to the reagent by means of the electrode reaction. Such a dosimeter is almost inexhaustible with respect to its reagent supply and is distinguished by a long service use. Potassium iodide is especially well suited as such a reagent. This reagent is well suited for detecting chloride. Furthermore, the potassium chloride leads to a blue coloration for the above-given reaction with the detection substance in the presence of starch. In this way, the person carrying the dosimeter can immediately recognize whether the substance to be detected is present and, if so, to judge from the degree of coloration in what amount the substance is present in order to initiate possible protective measures.

An improvement of the dosimeter is obtained by adding the reagent to the electrolyte in a dissolved form and to effect the mass transport decoupling between the electrodes by means of an ion exchange membrane. The reagent is especially mobile in the dissolved form so that only a very thin reaction front can form on the membrane. This assures approximately constant mass transport conditions during the measuring time. The ion exchanger membrane makes possible, on the one hand, a rapid exchange of the conducting electrolyte and, on the other hand, prevents a penetration of the reaction products to the counter electrode and thereby prevents an unwanted charge carrier exchange. A cationic exchanger on the basis of perfluorosulphonated PTFE has been found to be especially advantageous as a membrane material and is available in the marketplace under the trade name NAFION.

The ion exchanger membrane can preferably be either applied to the counter electrode at the electrolyte side or to the measuring electrode at the electrolyte side.

A further advantageous embodiment of the invention is obtained by providing a layer made of a conductive polymer on the measuring electrode. The detection substances diffusing through the membrane react with the polymer thereby causing the charge condition of the polymer to change. The changed charging condition forms quasi a non-mobile reaction product. Polyaniline has been found to be a suitable polymer.

The polymer can be supplemented with a catalyst as a reagent to further increase the electro-catalytic activity. Such a catalytic supplement is preferably ferrocen.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
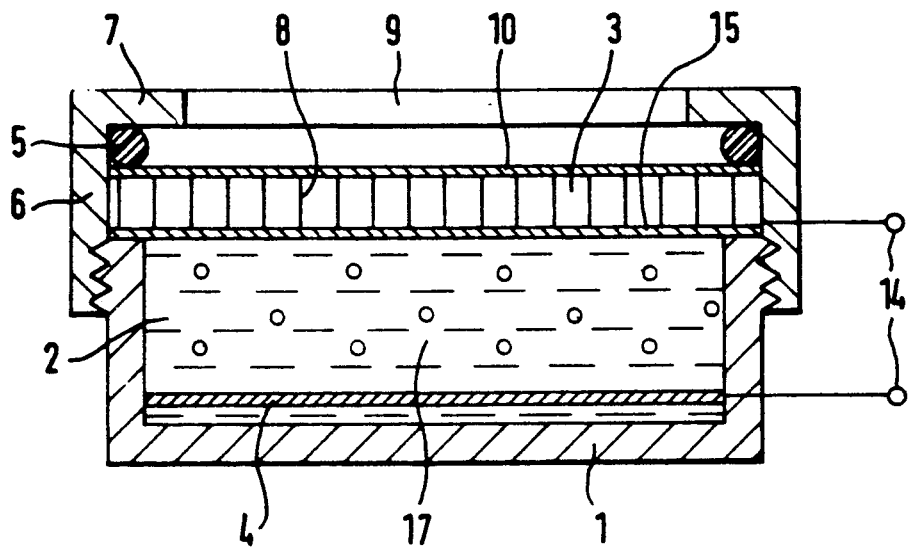
FIG. 1 is a side elevation view (not to scale) of an embodiment of a measuring cell according to the invention; and, FIG. 2 is a greatly enlarged broken-out portion of the measuring electrode of the measuring cell shown in FIG. 1.

In FIG. 1, a cup-shaped measuring cell housing 1 is filled with an electrolyte 2 which is disposed between a measuring electrode 3 and a counter electrode 4. The measuring electrode 3 is clamped over the open end of the measuring cell housing 1 and is pressed against the end face of the housing 1 by means of an O-ring 5. A clamping ring 6 is threadably attached to the housing 1 for maintaining the tension force and presses the measuring electrode 3 tightly against the end face of the measuring cell housing 1 with its collar 7.

A plurality of channels 8 extend through the measuring electrode 3 and connect the electrolyte 2 to the gas to be detected. This gas reaches the measuring electrode 3 covered with a membrane 10 through the opening 9 formed in the clamping ring 6. The channels 8 are represented by vertical lines because their small dimensions do not permit their illustration in FIG. 1. The measuring electrode 3 can comprise a honeycomb structure defining channels 8 having a hexagonal cross section and these channels 8 are formed from conductive material. Electrical terminals 14 from the measuring electrode 3 and the counter electrode 4 are lead out of the housing so that a measuring signal can be taken off and applied to an evaluation and indicating device (not shown).

The measuring electrode 3 is provided with an ion exchange membrane 15 at the electrolytic side for use as a sampling device. The ion exchange membrane prevents a mass transport between the electrodes (3, 4). The electrolyte 2 has a reagent 17 as an additive which is illustrated by small circles.

Figure 2:
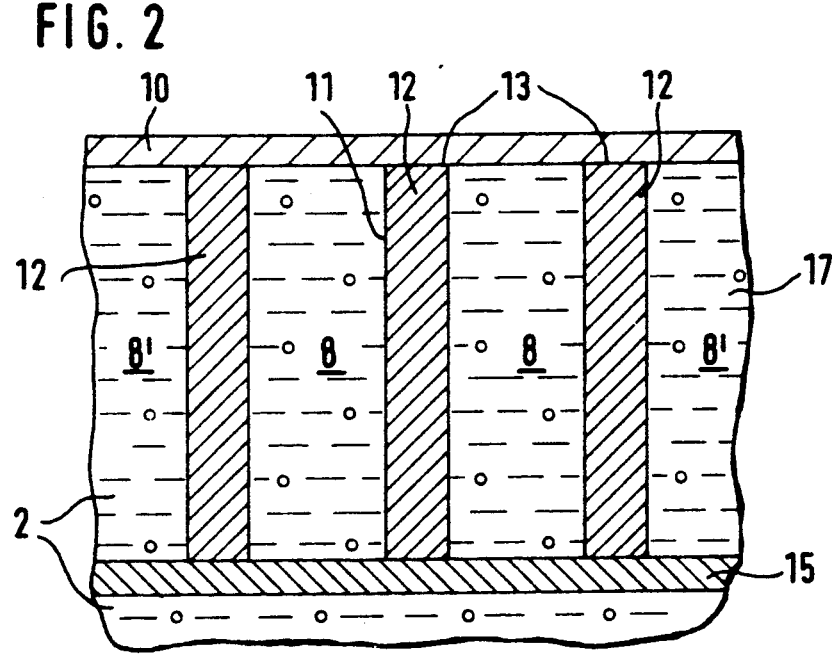

In FIG. 2, the greatly enlarged broken-out portion of the measuring cell of FIG. 1 shows two channels 8 of the measuring electrode 3 with its webs 12, end faces 13 and channel walls 11. The channels 8' adjacent the channels 8 are shown only incompletely; however, they continue on both sides of the channels 8 in a plurality of identical channels. The channels 8 have a wall length of approximately 300 micrometers and are completely filled with the electrolyte 2. The liquid electrolyte 2 has an additive in the form of a reagent 17 (shown by circles) and is filled as a mixture into the measuring cell housing wherein the counter electrode 4 is immersed.

It is understood that the foregoing description is that of the preferred embodiments of the invention and that various changes and modifications may be made thereto without departing from the spirit and scope of the invention as defined in the appended claims.

What is claimed is:

1. An electrochemical measuring cell for detecting a gas, the measuring cell comprising:
   a measuring electrode;
   a counter electrode;
   an electrolyte disposed between said electrodes;
   said measuring electrode including a web structure having a plurality of webs formed therein to define a plurality of gas permeable channels at least partially filled with said electrolyte; and,
   said web thickness being equal to or less than 5 micrometers and each of said channels having a diameter equal to or less than 10 micrometers and a length of up to 300 micrometers for said diameter.

2. The electrochemical measuring cell of claim 1, said length being up to 50 micrometers.

3. The electrochemical measuring cell of claim 1, wherein said channels are formed by a microstructure method which includes a lithographic method followed by galvanoforming.

4. The electrochemical measuring cell of claim 3, wherein said lithographic method is an X-ray lithographic method including synchrotron radiation.

5. The electrochemical measuring cell of claim 1, said webs having respective first end faces facing toward the ambient and respective second end faces facing toward said counter electrode; and, a hydrophobic coating formed on said channels in the region of said first end faces.

6. The electrochemical measuring cell of claim 5, said hydrophobic coating being a membrane placed over said channels.

7. The electrochemical measuring cell of claim 5, wherein said hydrophobic coating is deposited on said first end faces with the aid of the plasmapolymerization method so as to close off said measuring electrode with respect to the gas.

8. The electrochemical measuring cell of claim 1, comprising a reagent added to said electrolite for reacting with the gas to be detected.

9. The electrochemical measuring cell of claim 8, said reagent being a porphyrin complex.

10. The electrochemical measuring cell of claim 8, said reagent being selected from the group consisting of Fe-phthalocyanine complex and Co-phthalocyanine complex.

11. The electrochemical measuring cell of claim 10, each one of said channels being defined by a selected number of said webs which conjointly define an inner wall surface of said one channel; and, said reagent being applied to said inner wall surface.

12. The electrochemical measuring cell of claim 1, said measuring electrode and said counter electrode being made according to the same manufacturing method; and, said electrolyte being a polymer sandwiched between said electrodes.

13. The electrochemical measuring cell of claim 8, said electrolyte being selected so as to go into an irreversible reaction with said gas thereby permitting said cell to be used as a dosimeter; said channels having a length of approximately 200 to 300 micrometers; said webs having respective first end faces facing the ambient and respective second end faces facing toward said counter electrode; a poreless membrane placed over said first end faces to close off said channels; said electrodes being capable of being decoupled from each other with respect to a mass transport of said reagent and with respect to the primary reaction product formed with the detection substance; and, voltage means for applying a voltage across said electrodes after a sampling operation for quantitatively converting the reaction product into a secondary product by means of a redox reaction.

14. The electrochemical measuring cell of claim 13, wherein said reaction product is convertible into said reagent by means of said redox reaction.

15. The electrochemical measuring cell of claim 13, wherein said reagent is potassium iodide dissolved in a phosphate buffer.

16. The electrochemical measuring cell of claim 13, wherein said reagent is a catalytic additive bonded in a conductive polymer.

17. The electrochemical measuring cell of claim 16, wherein said catalytic additive is ferrocen.

18. The electrochemical measuring cell of claim 13, wherein said reagent is a conductive polymer.

19. The electrochemical measuring cell of claim 13, comprising an ion exchange membrane for decoupling said counter electrode from said measuring electrode with reference to said mass transport.

* * * * *

UNITED STATES PATENT AND TRADEMARK OFFICE
CERTIFICATE OF CORRECTION

PATENT NO. : 5,126,035
DATED : June 30, 1992
INVENTOR(S) : Herbert Kiesele, Jürgen Tewes, Wolfgang Ehrfeld and Dirk Schmidt It is certified that error appears in the above-identified patent and that said Letters Patent is hereby corrected as shown below:

In the title page, under "Assignee": delete "Dragerwerk Aktiengesellschaft" and substitute:
-- Dragerwerk Aktiengesellschaft, Lubeck; Kernforschungszentrum Karlsruhe GmbH, Egenstein-Leopoldshafen, Federal Republic of Germany--.

under "Assistant Examiner - Bruce F. Bell": insert -- Attorney - Walter Ottesen --.

In column 2, line 54: delete "on" and substitute -- in -- therefor.

In column 2, line 64: delete "as" and substitute -- is -- therefor.

In column 6, line 53: delete "electrolite" and substitute -- electrolyte -- therefor.

Signed and Sealed this

Fifth Day of October, 1993

Attest:

BRUCE LEHMAN

*Attesting Officer*                 *Commissioner of Patents and Trademarks*